US011874870B2

(12) United States Patent
Vaglio et al.

(10) Patent No.: US 11,874,870 B2
(45) Date of Patent: Jan. 16, 2024

(54) RHYTHMS OF LIFE

(71) Applicant: CERNER INNOVATION, INC., Kansas City, KS (US)

(72) Inventors: Jay Christopher Vaglio, Mission, KS (US); Matt Ryan Anderson, Kansas City, MO (US); Grant Taylor Floyd, Kansas City, KS (US); Anna-Therese Fowler, Leawood, KS (US); Alex Lende, Kansas City, MO (US); Mayur Rajendran, Overland Park, KS (US); Eric A. Wilson, Lee's Summit, MO (US)

(73) Assignee: Cerner Innovation, Inc., Kansas City, KS (US)

( * ) Notice: Subject to any disclaimer, the term of this patent is extended or adjusted under 35 U.S.C. 154(b) by 863 days.

(21) Appl. No.: 16/456,659

(22) Filed: Jun. 28, 2019

(65) Prior Publication Data
US 2020/0409994 A1 Dec. 31, 2020

(51) Int. Cl.
*G06F 16/638* (2019.01)
*G16H 10/60* (2018.01)

(52) U.S. Cl.
CPC ........... *G06F 16/639* (2019.01); *G16H 10/60* (2018.01)

(58) Field of Classification Search
None
See application file for complete search history.

(56) References Cited

U.S. PATENT DOCUMENTS

| 5,777,254 | A | * | 7/1998 | Fay | G10H 1/0058 |
| | | | | | 84/613 |
| 2011/0190595 | A1 | * | 8/2011 | Bennett | A61B 17/42 |
| | | | | | 600/301 |
| 2013/0039531 | A1 | * | 2/2013 | Basso | G06F 3/005 |
| | | | | | 382/103 |
| 2015/0057779 | A1 | * | 2/2015 | Saungsomboon | H04H 60/02 |
| | | | | | 700/94 |
| 2018/0032611 | A1 | * | 2/2018 | Cameron | G06F 16/685 |
| 2019/0371289 | A1 | * | 12/2019 | Alexanderson | G10H 1/0025 |

* cited by examiner

*Primary Examiner* — Thu N Nguyen
(74) *Attorney, Agent, or Firm* — Kilpatrick Townsend & Stockton LLP

(57) ABSTRACT

Embodiments of the present disclosure relate to systems, methods, and user interfaces for generating a soundtrack using integrated live data from an information system. In this way, the audio presentation for an organization can be automated utilizing meaningful data that is converted into unique sounds based on defined criteria that results in an almost endless culmination of songs providing a story unique to the organization. To do so, data is aggregated from a number of sources (e.g., analytics data, network activity, and the like). The data is converted into observables that can influence the selection of a base track comprising a measure of notes. A soundtrack is generated by applying the observables to the base track, the observables causing changes in one or more of the measure of notes, scale, tonic, tempo, or volume of the soundtrack.

20 Claims, 7 Drawing Sheets

RHYTHMS OF LIFE

BACKGROUND

Organizations are increasingly consolidating physical locations and, as a result, are building new structures and/or forming corporate offices. This trend often includes designing an experience for visitors, which includes visual and audio presentations. Some organizations provide the audio experience by utilizing licensed music, live performers, or pseudo-automated piano playing. Unfortunately, these options are often repetitive, require management, and do not provide any meaningful distinction from the audio experience of other organizations.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present disclosure relate to systems, methods, and user interfaces for generating a soundtrack using integrated live data from an information system. More particularly, embodiments of the present disclosure automate the audio presentation for an organization utilizing meaningful data that is converted into unique sounds based on defined criteria that results in an almost endless culmination of songs. In this way, a story unique to the organization can be presented by the audio presentation. To do so, data is aggregated from a number of sources (e.g., analytics data, network activity, and the like). The data is converted into observables that can influence the selection of a base track comprising a measure of notes. A soundtrack is generated by applying the observables to the base track, the observables causing changes in one or more of the measure of notes, scale, tonic, tempo, or volume of the soundtrack.

BRIEF DESCRIPTION OF THE SEVERAL VIEWS OF THE DRAWINGS

The present invention is described in detail below with reference to the attached drawing figures, wherein.

DETAILED DESCRIPTION

Figure 1:
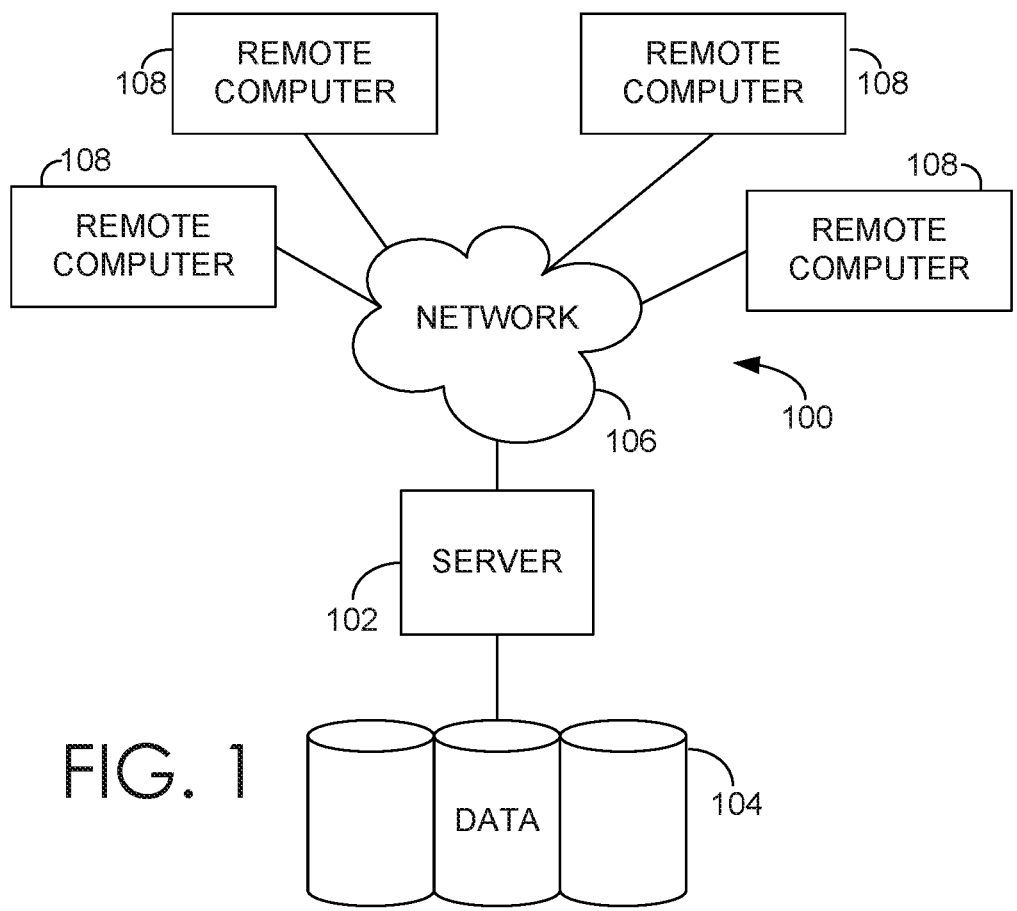
FIG. 1 is a block diagram of an exemplary operating environment suitable to implement embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" might be used herein to connote different elements of methods employed, the terms should not be interpreted as implying any particular order among or between various steps herein disclosed unless and except when the order of individual steps is explicitly stated.

As noted in the background, organizations are increasingly consolidating physical locations and, as a result, are building new structures and/or forming corporate offices. This trend often includes designing an experience for visitors, which includes visual and audio presentations. Some organizations provide the audio experience by utilizing licensed music, live performers, or pseudo-automated piano playing. Unfortunately, these options are often repetitive, require management, and do not provide any meaningful distinction from the audio experience of other organizations.

Embodiments of the present disclosure relate to systems, methods, and user interfaces for generating a soundtrack using integrated live data from an information system. More particularly, embodiments of the present disclosure automate the audio presentation for an organization utilizing meaningful data that is converted into unique sounds based on defined criteria that results in an almost endless culmination of songs. In this way, a story unique to the organization can be presented by the audio presentation. To do so, data is aggregated from a number of sources (e.g., analytics data, network activity, and the like). The data is converted into observables that can influence the selection of a base track comprising a measure of notes. A soundtrack is generated by applying the observables to the base track, the observables causing changes in one or more of the measure of notes, scale, tonic, tempo, or volume of the soundtrack.

Accordingly, one embodiment of the present disclosure is directed to one or more computer storage media having computer-executable instructions embodied thereon that, when executed by a computer, causes the computer to perform operations. The operations include receiving a selection of one or more base tracks comprising at least one measure of notes. The operations also include receiving data from one or more sources. The data comprises live data corresponding to an information system. The operations further include generating a soundtrack by applying observables corresponding to the data to the selection. Variations in the observables cause the scale, tonic, or tempo of the soundtrack to be modified.

In another embodiment, the present disclosure directed to a computerized method. The method comprises receiving data from one or more sources. The data comprises live data corresponding to an information system. The method also comprises, based on observables corresponding to the data, selecting a base track comprising a measure of notes. The method further comprises generating a soundtrack by applying the observables to the measure of notes. Variations in the observables cause the scale, tonic, or tempo of a synthesized instrument to be modified.

In yet another embodiment, the present disclosure is directed to a system. The system comprises a processor; and a computer storage medium storing computer-usable instructions that, when used by the processor, cause the processor to: receive data from one or more sources, the data comprising live data corresponding to an information system; convert the data into observables; based on the observables, select a base track comprising a measure of notes; and generate a soundtrack by applying the observables to the base track, the observables causing changes in one or more of the measure of notes, scale, tonic, tempo, or volume of the soundtrack.

Having briefly described embodiments of the present invention, an exemplary operating environment suitable for use in implementing embodiments of the present invention is described below. FIG. 1 provides an aspect of an example operating environment with which embodiments of the present invention may be implemented. The aspect of an operating environment is illustrated and designated generally as reference numeral 100.

Example operating environment 100 comprises a general purpose computing device in the form of a control server 102. Exemplary components of the control server 102 comprise a processing unit, internal system memory, and a suitable system bus for coupling various system components, including database cluster 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Control server 102 typically includes therein, or has access to, a variety of computer-readable media, for instance, database cluster 104. Computer-readable media can be any available media that might be accessed by control server 102, and includes volatile and nonvolatile media, as well as, removable and nonremovable media. Computer-readable media might include computer storage media. Computer storage media includes volatile and nonvolatile media, as well as removable and nonremovable media implemented in any method or technology for storage of information, such as computer-readable instructions, data structures, program modules, or other data. In this regard, computer storage media might comprise RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 102. Computer storage media does not comprise signals per se. Combinations of any of the above also may be included within the scope of computer-readable media.

The computer storage media discussed above and illustrated in FIG. 1, including database cluster 104, provide storage of computer-readable instructions, data structures, program modules, and other data for the control server 102. In some embodiments, data cluster 104 takes the form of a cloud-based data store, and in some embodiments is accessible by a cloud-based computing platform.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and providers' offices. Providers may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like.

The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Exemplary computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networked environment, program modules or portions thereof might be stored in association with the control server 102, the database cluster 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

In some embodiments, control server 102 is a computing system or platform made up of one or more computing devices. Embodiments of control server 102 may be a distributed computing system, a centralized computing system, a single computer such as a desktop or laptop computer or a networked computing system. Thus, in some embodiments, control server 102 comprises a multi-agent computer system with software agents.

Figure 2:
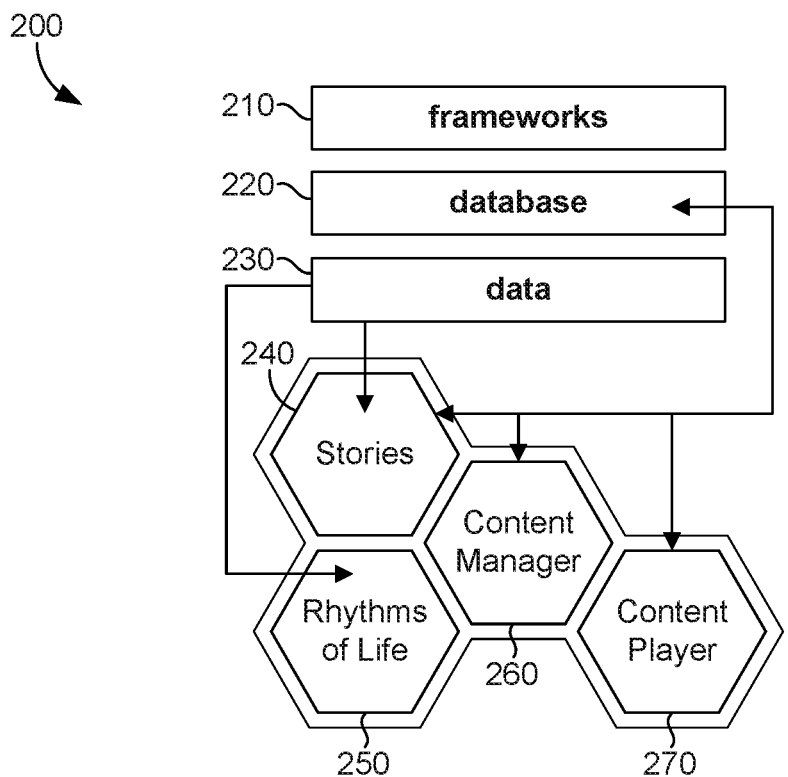
FIG. 2 depicts an exemplary framework of an internal server implementation of a Systems of Life system suitable to implement embodiments of the present invention.

Turning now to FIG. 2, an exemplary framework of an internal server implementation of a Systems of Life system 200 is shown, in accordance with an aspect of the present invention. It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. For instance, various functions may be carried out by a processor executing instructions stored in memory. The Systems of Life system 200 may be implemented via any type of computing device, such as computing device 100 described above with reference to FIG. 1, for example.

The Systems of Life system 200 generally operates to generate a soundtrack using integrated live data from an information system. More particularly, the Systems of Life system 200 automates the audio presentation for an organization utilizing meaningful data that is converted into unique sounds based on defined criteria that results in an almost endless culmination of songs. To do so, data is aggregated from a number of sources (e.g., analytics data, network activity, and the like). The data is converted into observables that can influence the selection of a base track comprising a measure of notes. A soundtrack is generated by applying the observables to the base track, the observables causing changes in one or more of the measure of notes, scale, tonic, tempo, or volume of the soundtrack.

As shown in FIG. 2, the Systems of Life system 200 includes, among other components not shown, frameworks 210, database 220, data source(s) 230, stories component 240, Rhythms of Life component 250, content manager 260, and content player 270. It should be understood that the Systems of Life system 200 shown in FIG. 2 is an example of one suitable computing system architecture. Each of the components shown in FIG. 2 may be implemented via any type of computing device, such as computing device 100 described with reference to FIG. 1, for example.

The components may communicate with each other via a network, which may include, without limitation, one or more local area networks (LANs) and/or wide area networks (WANs). Such networking environments are commonplace in offices, enterprise-wide computer networks, intranets, and the Internet. It should be understood that any number of databases or databases may be employed within the Systems of Life system 200 within the scope of the present disclosure. Each may comprise a single device or multiple devices cooperating in a distributed environment. For instance, each the stories component 240, the Rhythms of Life component 250, the content manager component 260, and the content player component 270 may be provided via multiple devices arranged in a distributed environment that collectively provide the functionality described herein. In other embodiments, a single device may provide the functionality of multiple components of the Systems of Life system 200. For example, a single device may provide the stories component 240, the Rhythms of Life component 250, the content manager component 260, and the content player component 270. Additionally, other components not shown may also be included within the network environment.

Frameworks 210 generally provide the tools that enable the soundtrack or stories to be generated. For example, in embodiments, React and Terra UI provide the tools for building the user interface of the Systems of Life system 200. Tone.js provides, in embodiments, the tools for creating base tracks utilized by the Systems of Life system 200. Cesium.js provides, in embodiments, the tools for creating visualizations of dynamic data. Rx.js provides, in embodiments, the tools for converting the data into observables, as described herein.

Database 220 generally is configured to store information for use by, for example, the stories component 240, the Rhythms of Life component 250, the content manager component 260, and the content player component 270. The information stored in association with database 220 is configured to be searchable for one or more items of information stored in association therewith. The information stored in association with the database 220 may comprise general information used by the Systems of Life system 200, the stories component 240, the Rhythms of Life component 250, the content manager component 260, and the content player component 270. For example, the information may be stories, soundtracks, base tracks, measures of notes, and the like that have been created to generate a soundtrack using integrated live data from an information system.

Data source(s) 230 generally provide data from a variety of source to be utilized by the Systems of Life system 200. The data may be information system data, such as data from a healthcare information system. Additionally or alternatively, the data may include external data, such as weather data provided by an API.

Figure 3:
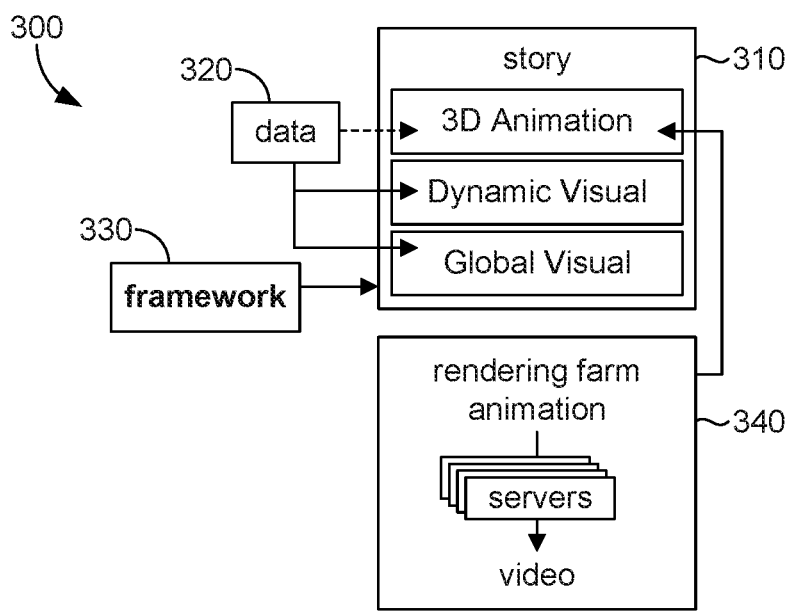
FIG. 3 depicts an exemplary framework of a stories component of the Systems of Life system suitable to implement embodiments of the present invention.

The stories component 240 generally provides visual content that is displayed to viewers. The content is data-driven visualizations that outline accomplishments of associates and collaborations with clients. The content may be dynamically created based on the data or informed by the data. As illustrated in FIG. 3 the stories component comprises visual component 310, data 320, framework 330, and video component 340.

Figure 4:
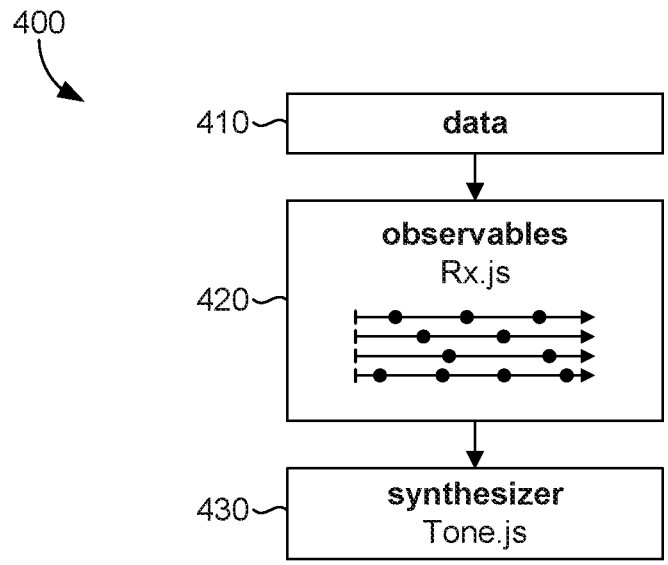
FIG. 4 depicts an exemplary framework of a rhythms component of the Systems of Life system suitable to implement embodiments of the present invention.

The Rhythms of Life component 250 generally provides audio content that supports the visual content provided by the stories component 240. The audio is procedurally generated based on the data as described herein. The Rhythms of Life component 250 enables a unique, one-of-a-kind, auditory experience to be created. The rhythm of life component 250 may be part of an integrated application of the Systems of Life system 200 or may be a standalone application. Turning briefly to FIG. 4, the Rhythms of Life component 250 comprises data 410, observables, 420 and a synthesizer 430, described in more detail below.

Figure 5:
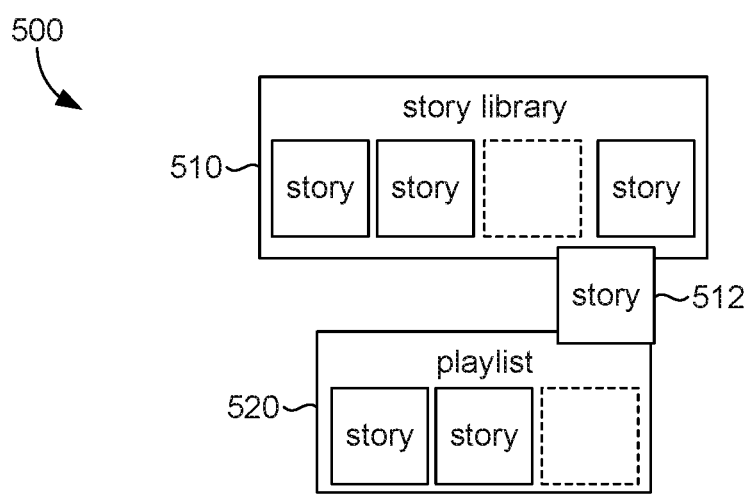
FIG. 5 depicts an exemplary framework of a content manager component of the Systems of Life system suitable to implement embodiments of the present invention.

The content manager 260 generally orchestrates all of the stories and audio content and enables a user to create custom playlists to assist in scheduling the Systems of Life 200 stories and audio for viewers and/or listeners. As shown in FIG. 5, the content manager 500 comprises story library 510 and playlist 520. As shown a particular story 512 can be added to a playlist from the story library 510 to create a particular ambience for the playlist. Although FIG. 5 is illustrated to show a playlist 520 of stories, it is also contemplated that the content manager 500 may comprise soundtracks, base tracks, or measures of notes.

Figure 6:
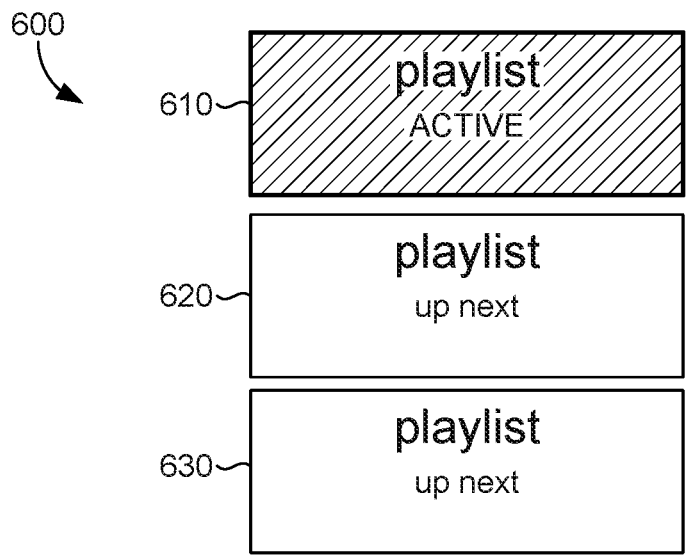
FIG. 6 depicts an exemplary framework of a content player component of the Systems of Life system suitable to implement embodiments of the present invention.

The content player 270 generally distributes the content to devices to display or play the playlists defined by the content manager 260. As illustrated in FIG. 6, the content player 600 comprises playlists 610, 620, 630. In embodiments, the playlists corresponding to periods of time (e.g., morning, afternoon, evening) and may comprise soundtracks that enhance the desired ambience for that particular period of time.

Figure 7:
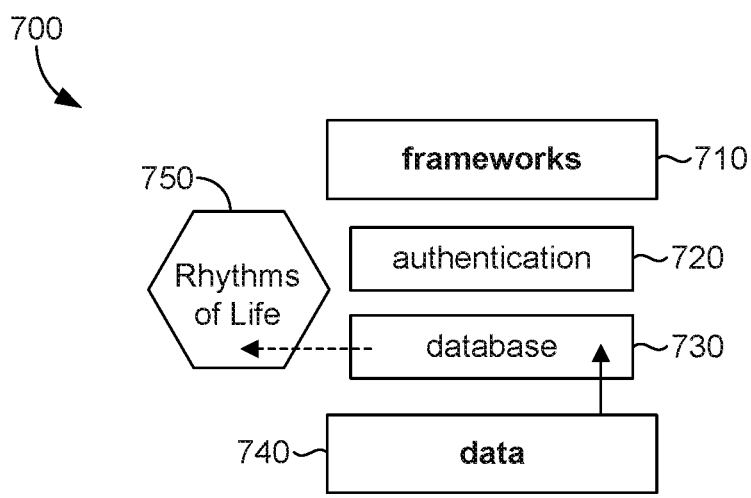
FIG. 7 depicts an exemplary framework of an external server implementation of a Systems of Life system suitable to implement embodiments of the present invention.

Referring now to FIG. 7, the external server implementation 700 of the Systems of Life system generally enables stories and/or audio content to be distributed to others (e.g., clients) without including the entire Systems of Life system 200 framework. Turning briefly to FIG. 7, the external server implementation 700 comprises frameworks 710, authentication component 720, database 730, data source 740.

Frameworks 710 generally provide the tools that enable the soundtrack or stories to be generated. For example, in embodiments, React and Terra UI provide the tools for building the user interface of the external server implementation 700 of the Systems of Life system. Tone.js provides, in embodiments, the tools for creating base tracks utilized by the external server implementation 700 of the Systems of Life system.

Authentication component 720 enables the rhythms of life component 750 to access and utilize the data stored in database 730. Database 730 generally is configured to store information for use by, for example, the Rhythms of Life component 750. The information stored in association with database 730 is configured to be searchable for one or more items of information stored in association therewith. The information stored in association with the database 730 may comprise general information used by the Rhythms of Life component 750. For example, the information may be stories, soundtracks, base tracks, measures of notes, and the like that have been created to generate a soundtrack using integrated live data from an information system. The information stored in association with the database 730 may be accessible by other systems (e.g., Rhythms of Life component 750 such as the Rhythms of Life component 250 of the internal server implementation 200 described with respect to FIG. 2).

Data source 740 generally provides data from a variety of source to be utilized by the external server implementation 700 of the Systems of Life system. The data may be information system data, such as data from a healthcare information. Additionally or alternatively, the data may include external data, such as weather data provided by an API.

In implementation, a base track is initially created, such as using one of the frameworks described above. The base track comprises at least one measure of notes. The notes are represented by a note index that numbers each note (e.g., 0-6) and defines each octave for each note. This enables the notes to be referred to by the Systems of Life system and varied based on observables. Additionally, instruments are represented by code (i.e., similar to changing settings on a software synthesizer) so the Systems of Life system can convert each note in the measure of notes into a sound (e.g. first sixteenth beat, second sixteenth beat, etc). After the data is read from the observables, the tones and the beats of the soundtrack can be played using the data. Additionally, different volumes, different base tracks, or effects to the instrument can also be defined. In this way, rather than having an actual instrument play the soundtrack, the instruments are actually created via code and driven by the data as it is received.

After the base track has been prepared, the complexity of the soundtrack is defined. Initially, observables that influences the selection of a particular base track is defined. Next, the timing for when each measure of notes of the base track is played is defined. Intervals for when each measure of notes switches (i.e., organically) can also defined. Additionally, conditional statements of change and conditions of scale, time, and tempo are defined.

Figure 8:
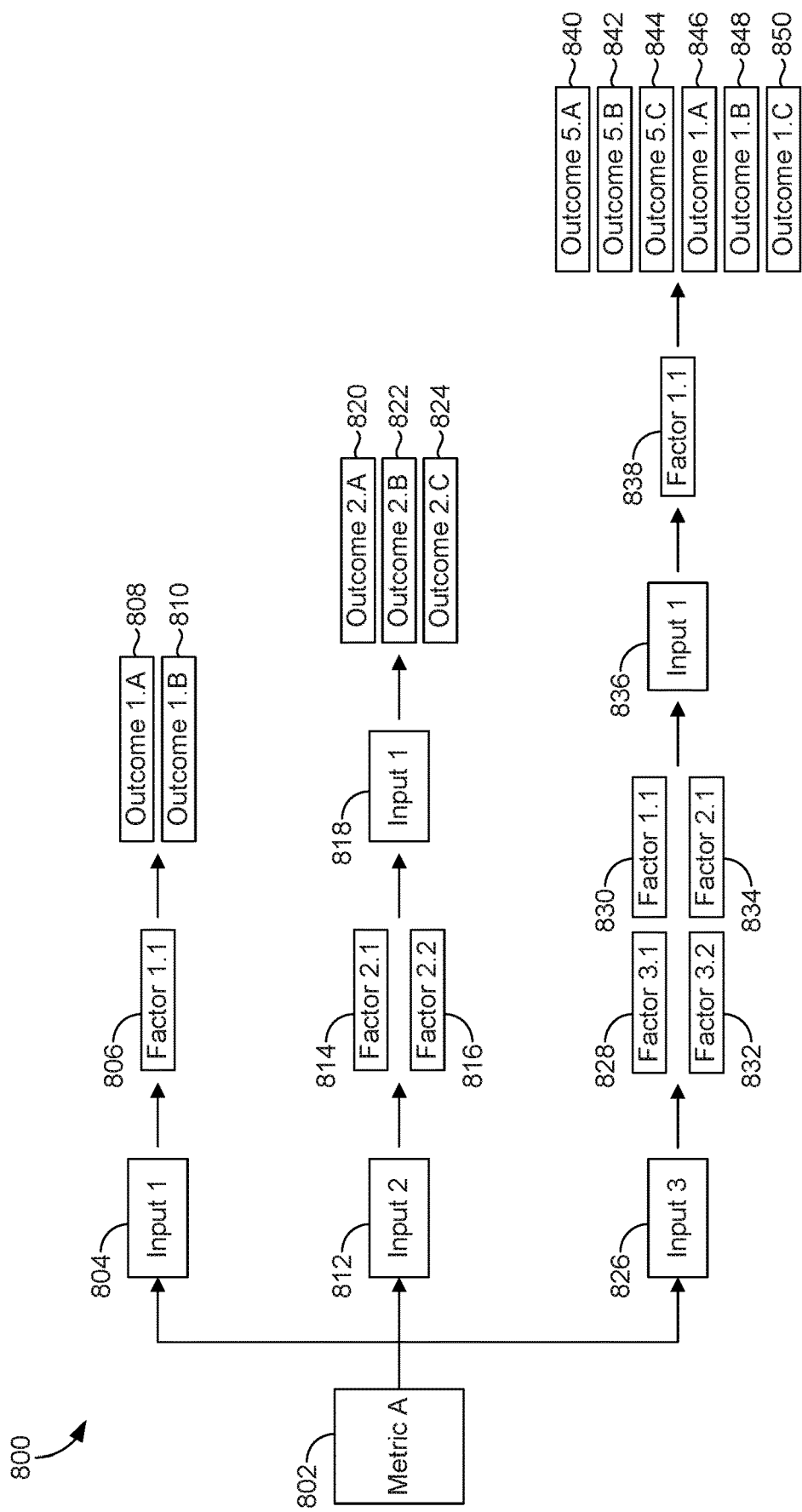
FIG. 8 depicts a flow diagram illustrating a method for converting the data to audio, in accordance with an embodiment of the present invention.

For example, with reference to FIG. 8, a flow diagram illustrating a method for converting the data to audio is provided, in accordance with embodiments of the present invention. Metric A 802 may represent a particular type of data corresponding to multiple inputs (e.g., Input 1 804, Input 2 812, and Input 3 826). In the context of a health information system, Metric A 802 may represent labor and delivery data, Input 1 804 may represent a female baby being born, Input 2 806 may represent a woman in labor being admitted that has not previously had a baby, and Input 3 826 may represent a woman in labor being admitted that has previously had a baby. Factors 806, 814, 816, 828, 830, 832, 834 may be applied to the inputs that, based on whether the data has increased or decreased from a previous time period, lead to a different outcome (i.e., a change in note, octave, etc.) When an observable indicating the baby is born (e.g., Input 1 818, Input 2 836), that observable can be used as a variable, or another factor may be applied (e.g., factor 806, 838) that may be based on the sex of the baby. Accordingly, a variety of outcomes 808, 810, 820, 822, 824, 840, 842, 844, 846, 848, and 850 create variations in the soundtrack. As can be appreciated, this decisional logic may be occurring for multiple measures of notes and multiple instruments at a time. Because the observables driving the outcomes (i.e., the sounds) may be received at different intervals, one instrument may play for a longer duration than another instrument.

Figure 9:
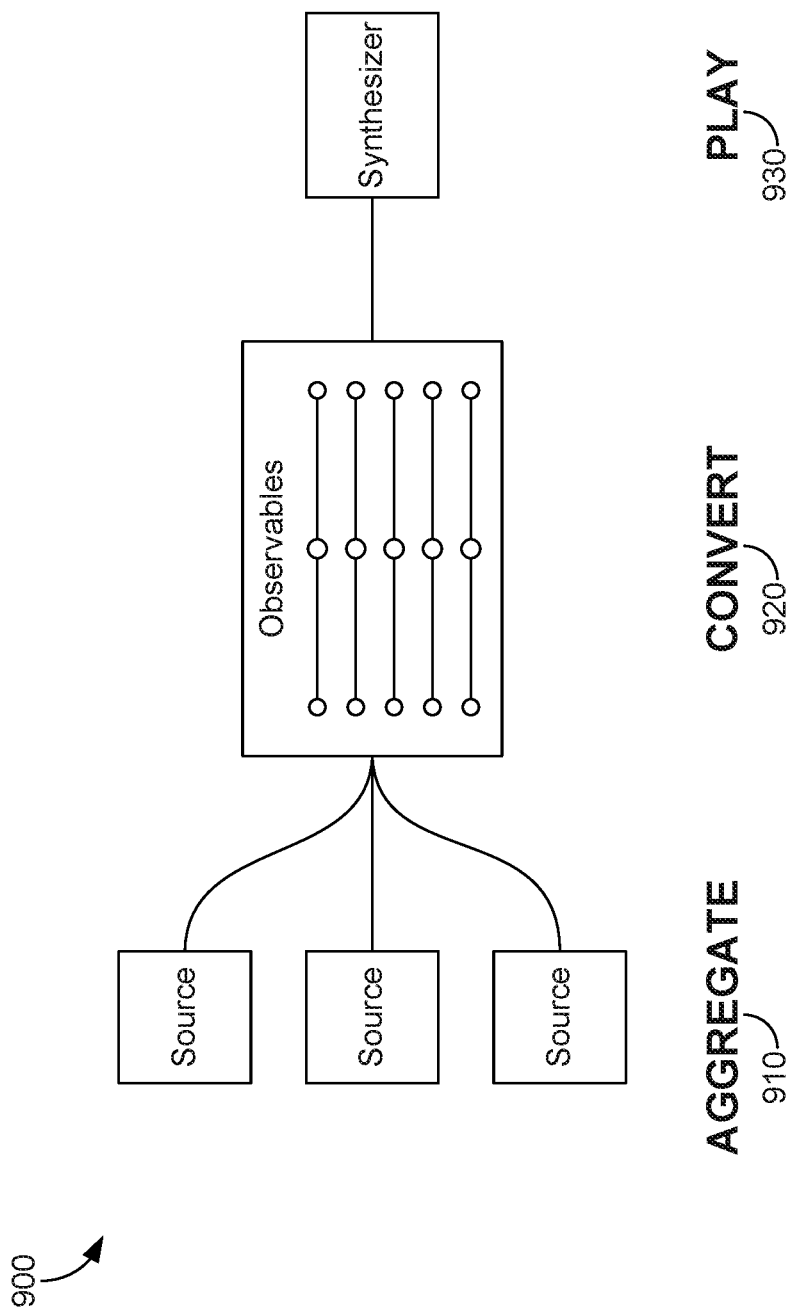
FIG. 9 depicts a flow diagram illustrating a method for generating a soundtrack using integrated live data from an information system, in accordance with an embodiment of the present invention.

Turning now to FIG. 9, a flow diagram is provided illustrating a method 900 for generating a soundtrack using integrated live data from an information system, in accordance with embodiments of the present invention. Method 900 may be performed by any computing device (such as computing device described with respect to FIG. 1) with access to an Systems of Life system (such as the one described with respect to FIGS. 2-7) or by one or more components of the Systems of Life system.

Initially, at step 910, an aggregation phase aggregates all data from each source of data. For example, data from multiple internal or external information systems can be aggregated and converted into observables. For clarity, an observable may indicate how particular data is interpreted and turned into a stream that is applied to conditions corresponding to a base track. In a healthcare information example, an observable may indicate a baby was born, a life has saved, or other events. Additionally, observables may be provided based on network activity, website visitors, or other events.

After the data is aggregated, observables within the data can be defined and/or identified, at step 920, in the conversion phase. The observables are abstractions in the data that can be utilized to alter the tracks or instruments using one or more of the frameworks described above (e.g., Reactive Extensions for JavaScript (RxJS)). Also in the conversion phase, the definitions for how the observables alter the tracks or instruments is defined. For example, the conditions that cause changes in the one or more measure of notes, scales, tonic, tempo, or volume of the soundtrack is defined.

Lastly, in the synthesizer phase, at step 930, the observables corresponding to the data are synthesized into audio by applying the observables to the selection (i.e., the base track or the measure of notes). As described herein, the observables or variations in the observables cause the scale, tonic, or tempo of the soundtrack to be modified. Additionally, the observables or variations in the observables can also cause a new base track or measure of notes to be selected. In some embodiments, other conditions such as time of day or day of the week may influence the selection of a base track or measure of notes.

In an example, a particular sound may be played three times in a row each time an observable corresponding to data is received. However, that observable may be received at various times throughout the day, so each time the observable is received, it may be applied to a different portion within the measure of notes or to a different base track. Accordingly, the soundtrack is unique because the observables within the live data may vary significantly.

In another example, a particular instrument may be synthesized as part of the soundtrack. That particular instrument may play each time an observable corresponding to data is received. However, the pitch or volume of that particular instrument may change if the observable was greater or less than the observable received the previous time that observable was received. As can be appreciated, the conditions and the variations in observables create an almost endless culmination of songs.

Figure 10:
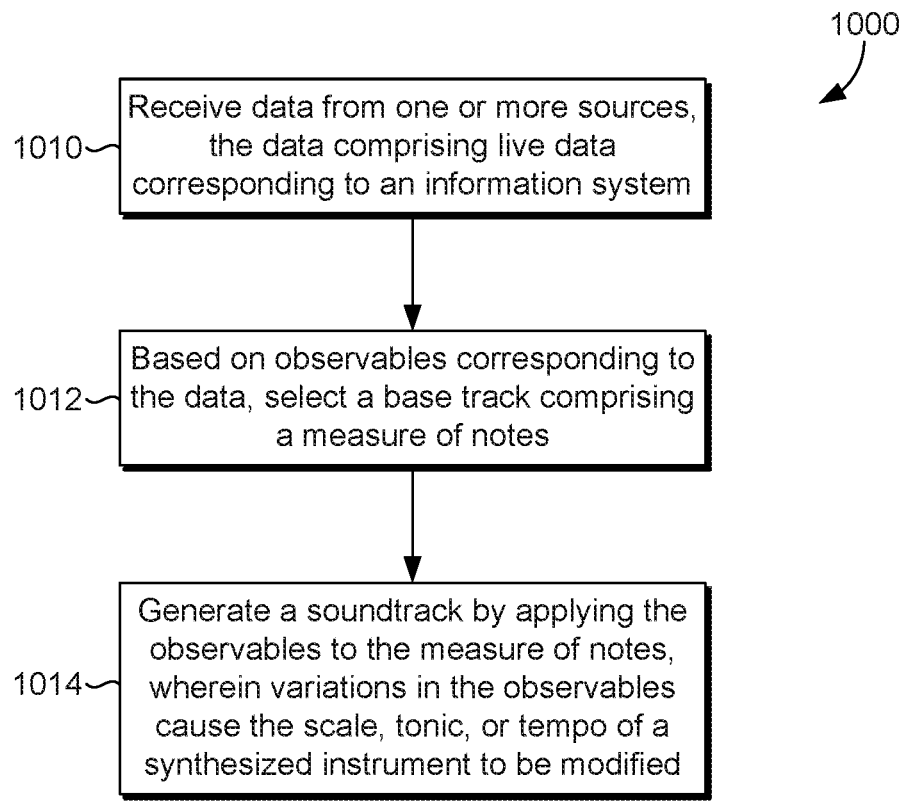
FIG. 10 depicts a flow diagram illustrating a method for generating a soundtrack utilizing live data corresponding to an information system, in accordance with an embodiment of the present invention.

Turning now to FIG. 10, a flow diagram is provided illustrating a method 1000 for generating a soundtrack utilizing live data corresponding to an information system, in accordance with embodiments of the present invention. Method 1000 may be performed by any computing device (such as computing device described with respect to FIG. 1) with access to an Systems of Life system (such as the one described with respect to FIGS. 2-7) or by one or more components of the Systems of Life system.

Initially, at step 1010, data is received from one or more sources. The data comprises live data corresponding to an information system. For example, the information system may be a healthcare information system. In another example, the information system may be an external system (e.g., weather data provided by an API). The data may be aggregated from the one or more sources. In some embodiments, the data is converted into observables (e.g., data meeting a particular threshold or value or a change in data over time, etc.).

Based on observables corresponding to the data, a base track comprising a measure of notes is selected, at step 1020. Notes of the measure of notes may be converted to a note index. The note index defines the variations in the scale, tonic, or tempo of the soundtrack that may be modified based on the observables.

In some embodiments, the synthesized instrument is selected based on an observable of the observables. In some embodiments, additional base tracks can be generated utilizing the one or more base tracks (i.e., machine learning).

A soundtrack is generated, at step 1030, by applying the observables to the measure of notes. As described herein, variations in the observables cause the scale, tonic, or tempo of a synthesized instrument to be modified.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. One or more computer storage media having computer-executable instructions embodied thereon that, when executed by a computer, causes the computer to perform operations, the operations comprising:
   receiving a selection of a base track comprising a first measure of notes;
   receiving data from one or more sources, the data comprising live data corresponding to an information system;
   converting the data into a plurality of observables, each observable corresponding to at least one note included in the first measure of notes;
   generating a soundtrack by applying the plurality of observables to the base track, the soundtrack comprising a second measure of notes, wherein at least one note included in the second measure of notes corresponds to a sound that is different from a sound corresponding to a note in the first measure of notes; and
   outputting the soundtrack using a synthesized instrument, wherein variations in a scale, tonic, or tempo of the synthesized instrument are modified based on the plurality of observables.

2. The media of claim 1, further comprising converting the data into the observables.

3. The media of claim 1, wherein the information system is a healthcare information system.

4. The media of claim 1, wherein the information system is an external system.

5. The media of claim 1, further comprising receiving a selection of an instrument to synthesize in accordance with the first measure of notes.

6. The media of claim 5, wherein the selection of the instrument is based on the observables.

7. The media of claim 1, further comprising generating one or more additional base tracks utilizing the base track.

8. The media of claim 1, further comprising aggregating the data from the one or more sources.

9. The media of claim 1, further comprising based on the observables, selecting a different base track or a different measure of notes of the first measure of notes.

10. The media of claim 1, further comprising converting notes of the first measure of notes to a note index.

11. The media of claim 10, wherein the note index defines the variations in the notes that are modified based on the observables.

12. A computerized method comprising:
   receiving a selection of a base track comprising a first measure of notes;
   receiving data from one or more sources, the data comprising live data corresponding to an information system;
   converting the data into a plurality of observables, each observable corresponding to at least one note included in the first measure of notes; and
   generating a soundtrack by applying the plurality of observables to the base track, the soundtrack comprising a second measure of notes, wherein at least one note included in the second measure of notes corresponds to a sound that is different from a sound corresponding to a note in the first measure of notes; and outputting the soundtrack using a synthesized instrument, wherein variations in the plurality of observables cause a scale, tonic, or tempo of the synthesized instrument to be modified.

13. The method of claim 12, wherein the synthesized instrument is selected based on an observable of the observables.

14. The method of claim 12, further comprising generating one or more additional base tracks utilizing the base track.

15. The method of claim 12, further comprising aggregating the data from the one or more sources.

16. The method of claim 15, further comprising converting the data into the observables.

17. The method of claim 12, wherein the information system is a healthcare information system.

18. The method of claim 12, wherein the information system is an external system.

19. The method of claim 12, further comprising converting notes of the first measure of notes to a note index, wherein the note index defines the variations in the notes that are modified based on the observables.

20. A system comprising:
a processor; and
a computer storage medium storing computer-usable instructions that, when used by the processor, cause the processor to:
receive a selection of a base track comprising a first measure of notes;
receive data from one or more sources, the data comprising live data corresponding to an information system;
convert the data into a plurality of observables, each observable corresponding to at least one note included in the first measure of notes;
generate a soundtrack by applying the plurality of observables to the base track, the soundtrack comprising a second measure of notes, wherein at least one note included in the second measure of notes corresponds to a sound that is different from a sound corresponding to a note in the first measure of notes; and
outputting the soundtrack using a synthesized instrument, the observables causing changes in a scale, tonic, tempo, or volume of the synthesized instrument.

* * * * *